United States Patent [19]

Frosch et al.

[11] 4,243,327
[45] Jan. 6, 1981

[54] DOUBLE-BEAM OPTICAL METHOD AND APPARATUS FOR MEASURING THERMAL DIFFUSIVITY AND OTHER MOLECULAR DYNAMIC PROCESSES IN UTILIZING THE TRANSIENT THERMAL LENS EFFECT

[76] Inventors: Robert A. Frosch, Administrator of the National Aeronautics and Space Administration, with respect to an invention of Frosch; Jovan Moacanin, Los Angeles; Amitava Gupta, Pasadena; Su-don Hong, Temple City, all of Calif.

[21] Appl. No.: 8,211

[22] Filed: Jan. 31, 1979

[51] Int. Cl.³ ............................................. G01N 21/01
[52] U.S. Cl. .................................. 356/432; 73/15 R
[58] Field of Search ............... 356/128, 256, 432, 436; 350/179, 180; 73/15 A, 15 R

[56] References Cited

PUBLICATIONS

Twarowski, A. J. et al., "Multiphoton Absorption Spectra Using Thermal Blooming", Chem. Physics 20, (1977), pp. 253–258.
Buser, A. G. et al., "Transient Thermal Blooming of Single and Multiple Short Laser Pulses", Applied Optics, vol. 14, No. 11, Nov. 1975, pp. 2740–2742.
Sooy, W. R. et al., "Switching Semiconductor Reflectivity by a Giant Pulse Laser", Applied Physics Letters, vol. 5, No. 3, pp. 54–56, Aug. 1964.
Pridmore-Brown "Absorption Saturation Effects on High-Power CO₂ Laser Beam Transmission", Applied Optics, vol. 12, No. 9, Sep. 1973, pp. 2188–2191.
Hu et al., "Now Thermooptical Measurement Method and a Comparison with Other Methods", Applied Optics, vol. 12, No. 1, Jan. 1973 pp. 72–79.

*Primary Examiner*—Paul A. Sacher
*Assistant Examiner*—Bruce Y. Arnold
*Attorney, Agent, or Firm*—Monte F. Mott; John R. Manning; Wilfred Grifka

[57] ABSTRACT

A method and apparatus for measuring thermal diffusivity and molecular relaxation processes in a sample material utilizing two light beams, one being a pulsed laser light beam for forming a thermal lens in the sample material, and the other being a relatively low power probe light beam for measuring changes in the refractive index of the sample material during formation and dissipation of the thermal lens. More specifically, a sample material is irradiated by relatively high power, short pulses from a dye laser. Energy from the pulses is absorbed by the sample material, thereby forming a thermal lens in the area of absorption. The pulse repetition rate is chosen so that the thermal lens is substantially dissipated by the time the next pulse reaches the sample material. A probe light beam, which in a specific embodiment is a relatively low power, continuous wave (cw) laser beam, irradiates the thermal lens formed in the sample material. The intensity characteristics of the probe light beam subsequent to irradiation of the thermal lens is related to changes in the refractive index of the sample material as the thermal lens is formed and dissipated. A plot of the changes in refractive index as a function of time during formation of the thermal lens as reflected by changes in intensity of the probe beam, provides a curve related to molecular relaxation characteristics of the material, and a plot during dissipation of the thermal lens provides a curve related to the thermal diffusivity of the sample material.

16 Claims, 10 Drawing Figures

DOUBLE-BEAM OPTICAL METHOD AND APPARATUS FOR MEASURING THERMAL DIFFUSIVITY AND OTHER MOLECULAR DYNAMIC PROCESSES IN UTILIZING THE TRANSIENT THERMAL LENS EFFECT

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

FIELD OF THE INVENTION

The invention relates to apparatus and methods for measuring molecular relaxation characteristics and thermal diffusivity of a sample material, and more particularly to measurement of these characteristics through use of thermooptical apparatus and techniques.

BACKGROUND OF THE INVENTION

Conventional apparatus and methods for the measurement of thermal diffusivity of solids generally require application of heat at a point in the solid using some type of heater, and then measurement of temperature rises as a function of time at several points within the solid using an appropriate temperature measuring device such as a thermistor. Recent developments in thermooptical techniques include use of a pulsed laser beam to supply heat to the sample material. However, temperature measurements are still generally made using thermistors or other conventional devices. In one method, a single laser beam is used to both form the thermal lens and to monitor the change of refractive index in a sample material. This single beam technique utilized a helium/neon laser whose output was periodically interrupted with a mechanical shutter. Use of a single beam, although superior to many conventional methods, has limited resolution capability because the measurement beam is also the beam supplying heat to the sample material.

Problems associated with conventional methods for measuring thermal properties of a material are many and varied. Typically, a relatively large sample is required, and it is difficult to perform a measurement under quasi-isothermal conditions since temperature gradients of less than 0.01° Kelvin per centimeter cannot be measured with precision. It is also difficult to adapt conventional techniques to samples under stress or to samples undergoing various other types of test environments. Conventional techniques tend to be slow, and transient changes in thermal properties cannot be measured utilizing conventional measurement apparatus. In addition, conventional techniques do not provide any way to directly measure rates of lattice relaxation processes in polymers and composites or to accurately measure anisotropic thermal properties or thermal properties of a surface of a material. An apparatus and method according to the present invention solves all of the above problems associated with conventional measurement techniques.

SUMMARY OF THE INVENTION

The invention provides an apparatus and method for measuring thermal diffusivity and molecular relaxation characteristics of a sample material. An apparatus according to the invention utilizes two light beams, one of which is used to form the thermal lens and the other of which is used to monitor changes in the refractive index of the material comprising the thermal lens during formation and dissipation of the thermal lens. The invention provides a pulsed laser light source, which in a specific embodiment is a dye laser, the light source providing a light beam directed at the sample material for formation of the thermal lens therein. The pulsed laser wavelength is chosen so that its energy will be partially absorbed by the sample material. A probe light beam source, which in a specific embodiment is a low power continuous wave (cw) laser, provides a probe light beam which is directed to irradiate the thermal lens and which either passes through the thermal lens if the material is substantially transparent to the probe light beam wavelength, or is reflected from the thermal lens if the material is substantially opaque to the probe light beam wavelength. The probe light laser beam does not deposit any significant energy in the sample material. The intensity of a portion of the probe light beam after having irradiated the thermal lens is related to the refractive index of the thermal lens. An intensity versus time profile of the probe light beam is related to the change in refractive index of the material comprising the thermal lens. Thus, one can appreciate that the rate of formation of the thermal lens as determined by changes in the refractive index of the sample material comprising the thermal lens is related to molecular relaxation characteristics of the sample material, and the rate of dissipation of the thermal lens as determined by changes in the refractive index is related to the thermal diffusivity of the sample material. A combining of the intensity versus time profiles of the probe light beam for a plurality of thermal lenses, each being formed by one of the pulses for the pulsed laser light source, provides a composite profile which accurately reflects the characteristics of the sample material.

Through use of the methods and apparatus provided by the invention, and a suitable choosing of the characteristics of the pulsed laser forming the thermal lens, a very small sample volume can be utilized. It is theorized that the volume of the thermal lens created by the apparatus disclosed herein is equal to or less than $10^{-5}$ cubic centimeters and that accurate measurement of temperature gradients less than $10^{-3}$ degrees Kelvin per cm can be made. The apparatus provides a means for making non-destructive tests using both isotropic and anisotropic materials which can be either transparent or opaque to the light sources being utilized. In addition, thermal diffusivity and molecular relaxation characteristics can be measured using a sample undergoing stress tests or a sample which is shock sensitive.

DETAILED DESCRIPTION

As required, detailed illustrative embodiments of the invention are disclosed herein. These embodiments exemplify the invention and are currently considered to be the best embodiments for such purposes. However it is to be recognized that other means exist for directing the pulsed laser light beam to a sample material for formation of a thermal lens therein, and other means for directing the probe light beam to the thermal lens could be utilized. Accordingly, the specific embodiments disclosed are representative in providing a basis for the claims which define the scope of the present invention.

As previously explained, the invention provides an apparatus and method for measuring thermal diffusivity and molecular relaxation characteristics of a sample material. A pulsed laser light beam is directed at a sample material, energy transfer from the laser light source to the material creating a thermal lens therein. A second continuous wave probe light beam is directed at the thermal lens, the intensity per unit area of the probe light beam being altered by the thermal lens regardless of whether the probe light beam is transmitted through or reflected from the thermal lens. The intensity of the probe light beam varies as the index of refraction of the sample material changes due to creation of the thermal lens. A change in the index of refraction during the formation of the thermal lens is related to the molecular relaxation characteristics of the sample material, and the change in the index of refraction during dissipation of the thermal lens is related to the thermal diffusivity of the sample material. Thus it is the altering of the probe light beam intensity characteristics due to index of refraction changes during the formation of and dissipation of a thermal lens formed by the pulsed laser light beam which provides a means for determining molecular relaxation characteristics and thermal diffusivity of the sample material.

Figure 1:
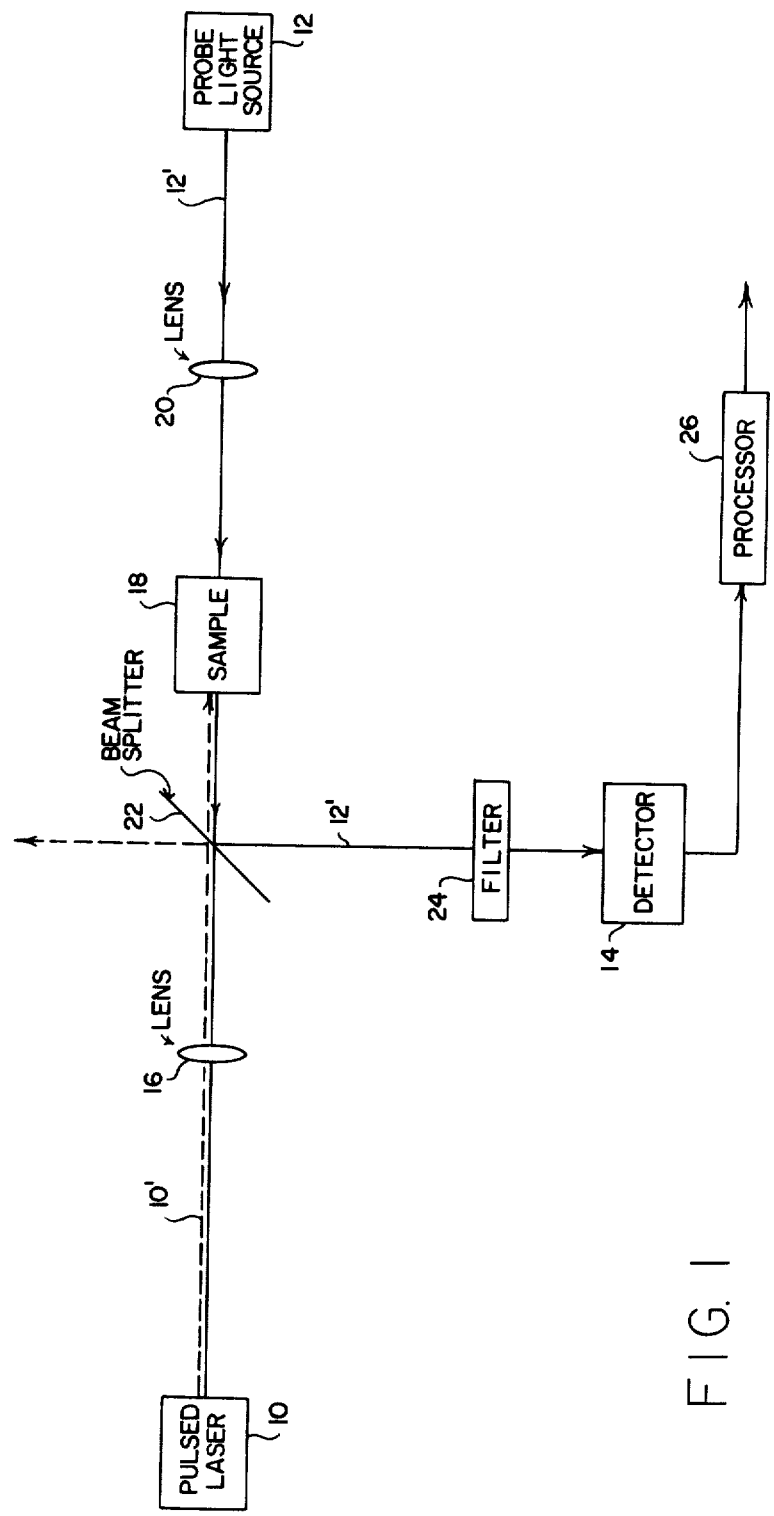
FIG. 1 is a schematic diagram of a first embodiment according to the invention in which the sample material is substantially transparent to the pulsed laser light beam and the probe laser light beam.

Referring to FIG. 1, an apparatus according to the invention comprises a pulsed laser light source 10 which provides a pulsed laser light beam 10', a probe light source 12 which provides a probe light beam 12', and a detector 14. A pulsed laser light beam focusing lens 16 is provided to focus the pulsed laser light beam 10' at an appropriate point within a sample material 18 where a thermal lens is to be formed. In the first embodiment shown in FIG. 1, the sample material 18 is of a type substantially transparent to both the pulsed laser light beam 10' and the probe light beam 12'. The focal point of the pulsed laser lens 16 is chosen to be within the sample material 18 where thermal diffusivity or molecular relaxation characteristics are to be determined. A probe light beam focusing lens 20 is provided for concentrating the probe light beam 12' on an area defined by the thermal lens. Choosing of the focal point for the probe laser focusing lens 20 is determined in accordance with whether or not the probe light beam as a result of passing through the thermal lens formed in the sample material 18 is to become less intense or more intense and will be explained in further detail below. A beam splitter 22 is positioned so that the probe light beam 12' having passed through the thermal lens formed in the sample material is reflected to the detector 14. A pulsed laser light beam filter 24 is provided in front of the detector 14 so that any pulsed laser light reflected back along a path colinear with that of the original pulsed laser light beam 10' will be prevented from reaching the detector 14, the pulsed laser light beam 10' having significantly more power than the probe light beam 12' as will be explained below. A processor 26 receives the output of the detector 14, the processor providing a means for forming a composite profile comprising successive intensity v. time profiles of the probe light beam 12' during formation and dissipation of the thermal lenses created by successive laser light pulses from the pulsed laser light source 10.

In the first embodiment, as in subsequent embodiments to be described below, the probe light source 12 is a continuous wave (cw) laser. Although a laser has been chosen for the probe light source 12, an incandescent or any other continuous light source could be utilized, the only requirement being that the light source be sufficiently focused so that intensity changes as a result of the formation of a thermal lens having a volume less than $10^{-5}$ cubic centimeters can be measured. It has been found that use of a cw laser for the probe light source 12 is particularly suitable for the type of application described herein. However, the cw laser comprising the probe light source 12 must be of sufficiently low power so that it does not deposit any significant energy in the sample material 18 as it passes therethrough. Immediately after a pulse from the pulsed laser light source 10 is partially absorbed in the sample material 18, a lattice distortion occurs in the region of energy absorption, thereby resulting in a decrease in the index of refraction in the region of distortion. It is this decrease in index of refraction that defines the region of the thermal lens. The probe light beam 12' as it passes through the thermal lens exhibits an intensity change due to the altered index of refraction. It is this intensity change that is detected by the detector 14. The intensity versus time profiles as a result of each of the laser pulses are combined by the processor 26 to provide a composite intensity versus time profile which is related to changes in the index of refraction of the sample material 18 comprising the thermal lens. As previously explained, the rate of formation of the thermal lens is related to molecular relaxation characteristics of the sample material 18. Following formation of the thermal lens, the lens then dissipates gradually as heat is transported away from the sample material comprising the thermal lens. The dissipation time of the thermal lens is thus related to the thermal diffusivity of the sample material, the time being determined by measuring changes in the index of refraction of the sample material as indicated by changes in intensity of the probe light beam 12' monitored by the detector 14.

Figure 2A:
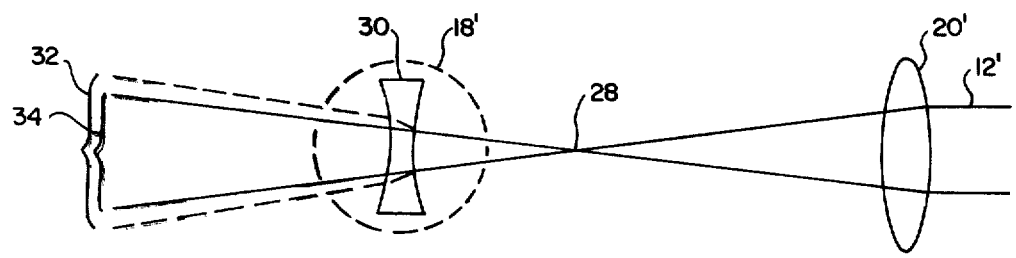
FIG. 2A is a ray-trace diagram showing the probe light beam focused at a point in front of the thermal lens formed in the sample material.
Figure 2B:
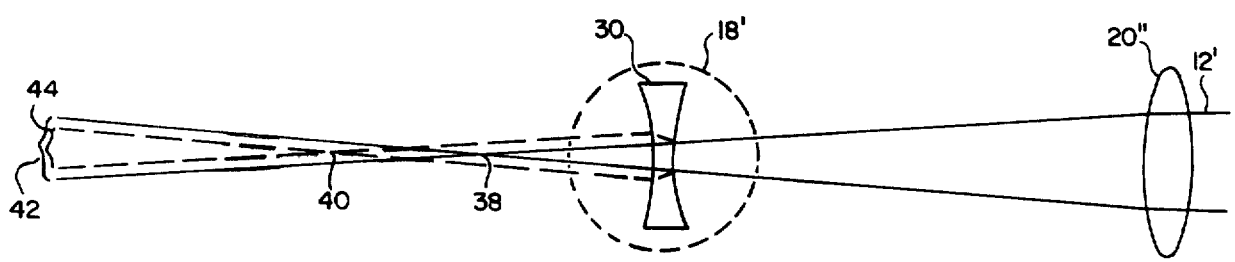
FIG. 2B is a ray-trace diagram showing the probe light beam focused at a point behind the thermal lens formed in the sample material.

An increase or decrease in the intensity of the probe light beam 12' as it passes through the thermal lens can be chosen according to the focal length of the probe light beam focusing lens 20. Referring to FIG. 2A, the probe light beam 12' is focused by a probe light beam focusing lens 20' having a focal point 28 located between the focusing lens 20' and a thermal lens 30 formed in a portion of the sample material 18' as represented by the dotted lines. As can be seen, the beam area as represented at 32 is larger as a result of the beam passing through the thermal lens 30 than it would be had the thermal lens not been formed as represented at 34. It should be noted from reference to FIG. 2A that the thermal lens 30 created by the pulsed laser light beam 10' can be represented schematically by a convex lens. Referring to FIG. 2B, if a focal point of a probe light beam focusing lens 20" is chosen to be at a point subsequent to the probe light beam 12' having passed through the thermal lens 30 as shown at 38, then the thermal lens 30 will cause the focal point to shift away from the probe light source 12 as represented at 40. This shift in focal point results in an area subscribed by the original and unaffected probe light beam 12' as shown at 42 being larger than that of the probe light beam 12' as affected by the thermal lens 30 as shown at 44. Thus as one can appreciate from the above explanation, the intensity of the probe light beam 12' having passed through the thermal lens 30 decreases when the focal point occurs prior to the thermal lens 30 as shown in FIG. 2A, and increases when the focal point occurs beyond the thermal lens 30 as shown in FIG. 2B.

Figures 3A, 3B, 3C:
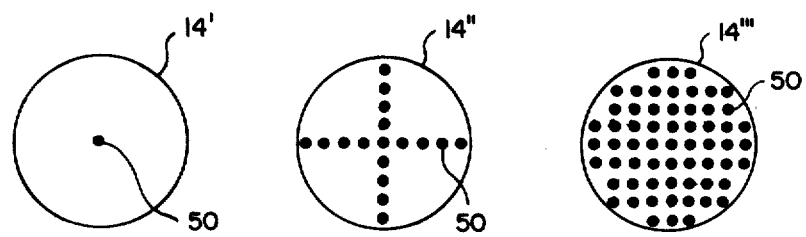
FIG. 3A is a schematic diagram showing a detector configuration comprising a single photodiode or photon counter.
FIG. 3B is a schematic diagram showing a detector configuration comprising a plurality of photodiode detectors positioned along two lines forming a cross.
FIG. 3C is a schematic diagram showing a detector configuration comprising a plurality of photodiode detectors uniformly positioned with respect to each other over a circular area.

The detector 14 can consist of a variety of configurations depending upon the accuracy to which the characteristics of the forming and dissipating thermal lens are desired to be known. The detector 14 could be of any type which would provide an output signal related to the intensity of the probe light beam 12' by which it is irradiated. Each detecting element could comprise a photodiode or photon counter, although any light sensitive detecting element having sufficient sensitivity could be utilized. Referring to FIG. 3A, a first detector configuration 14' comprises a single detecting element 50. A second detector configuration 14" comprising a plurality of detecting elements 50 in the form of a cross is shown in FIG. 3B, this configuration being used to detect both vertical and horizontal intensities of the probe light beam 12'. A preferred detector configuration for determining thermal diffusivity is shown in FIG. 3C in which the detecting elements 50 are disposed so as to cover the entire area of the detector 14''' being irradiated by the probe light beam 12'. This type of detector 14''' is commonly known as an area sensitive optical multichannel analyzer and provides a plurality of outputs each associated with one detector element 50. Use of this detector configuration 14''' will provide a plurality of intensity versus time profiles, thereby providing an extremely accurate means for determining the thermal diffusivity of the sample material.

Figure 4:
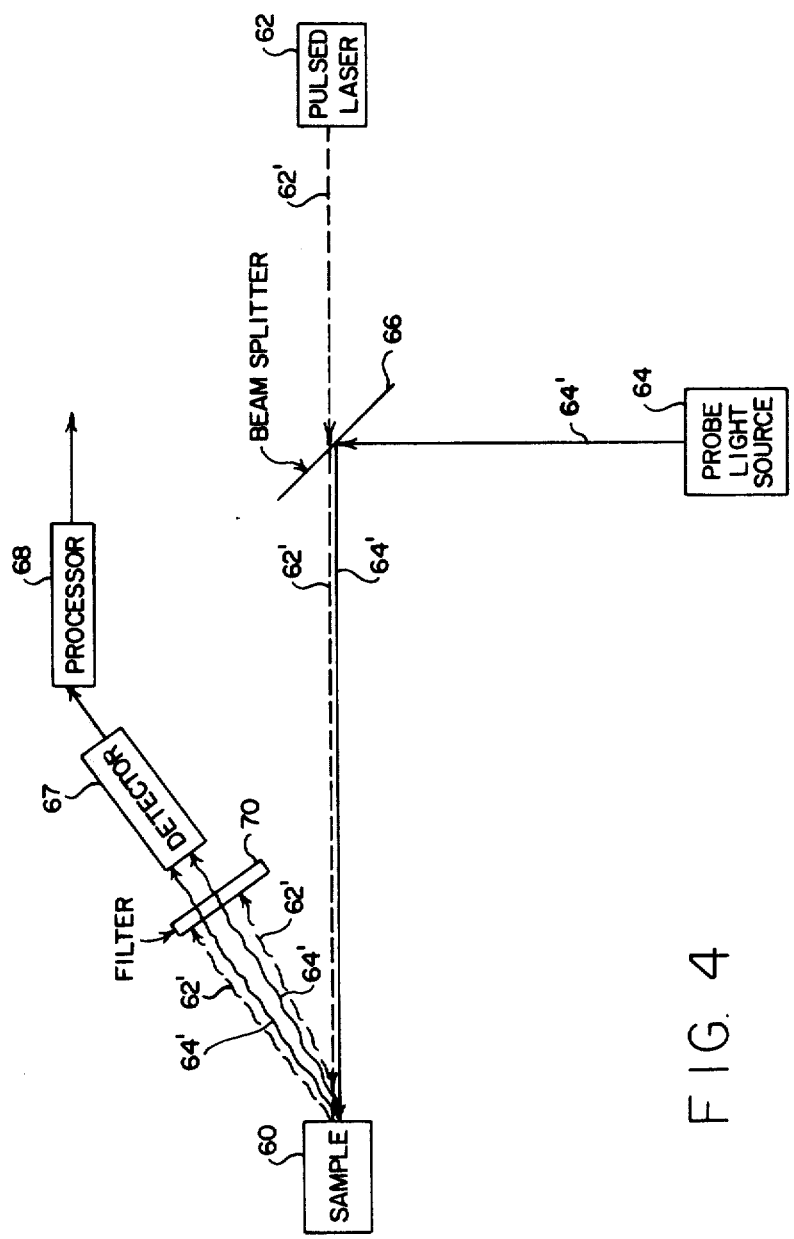
FIG. 4 is a schematic diagram of a second embodiment according to the invention in which the sample material is substantially opaque to the pulsed laser light beam and the probe light beam, and the probe light beam is reflected from the sample material directly to the detector.

A second embodiment of the invention is shown in FIG. 4. A sample material 60 comprises a material which is opaque to both a pulsed laser light beam and a probe light beam. Referring to FIG. 4, a pulsed laser light source 62 providing a pulsed laser light beam 62' is directed at the sample material 60. A probe light source 64 provides a probe light beam 64' which is partially reflected by a beam splitter 66 so that the reflected portion is colinear with the pulsed laser light beam 62'. The pulsed laser in this embodiment is chosen to be a dye laser having a wavelength such that its energy is partially absorbed within a few microns of the surface of the sample material 60. The thermal lens formed by the pulsed laser light beam 62' is therefore within a few microns of the surface of the sample material 60 and results in a reflection of the probe light beam 64' having an altered intensity with respect to what it would otherwise have been had the thermal lens not been formed in the sample material 60. This reflected probe light beam 64' is detected by a detector 67, the intensity versus time output profiles corresponding to successive laser pulses being converted by a processor 68 to form composite intensity versus time profiles as previously explained. A pulsed laser filter 70 is also provided, the filter 70 being chosen to substantially block the pulsed laser light beam 62'. As in the first embodiment, the detector 66 can have any of the configurations as previously explained in conjunction with the discussion relating to FIG. 3.

Figure 5:
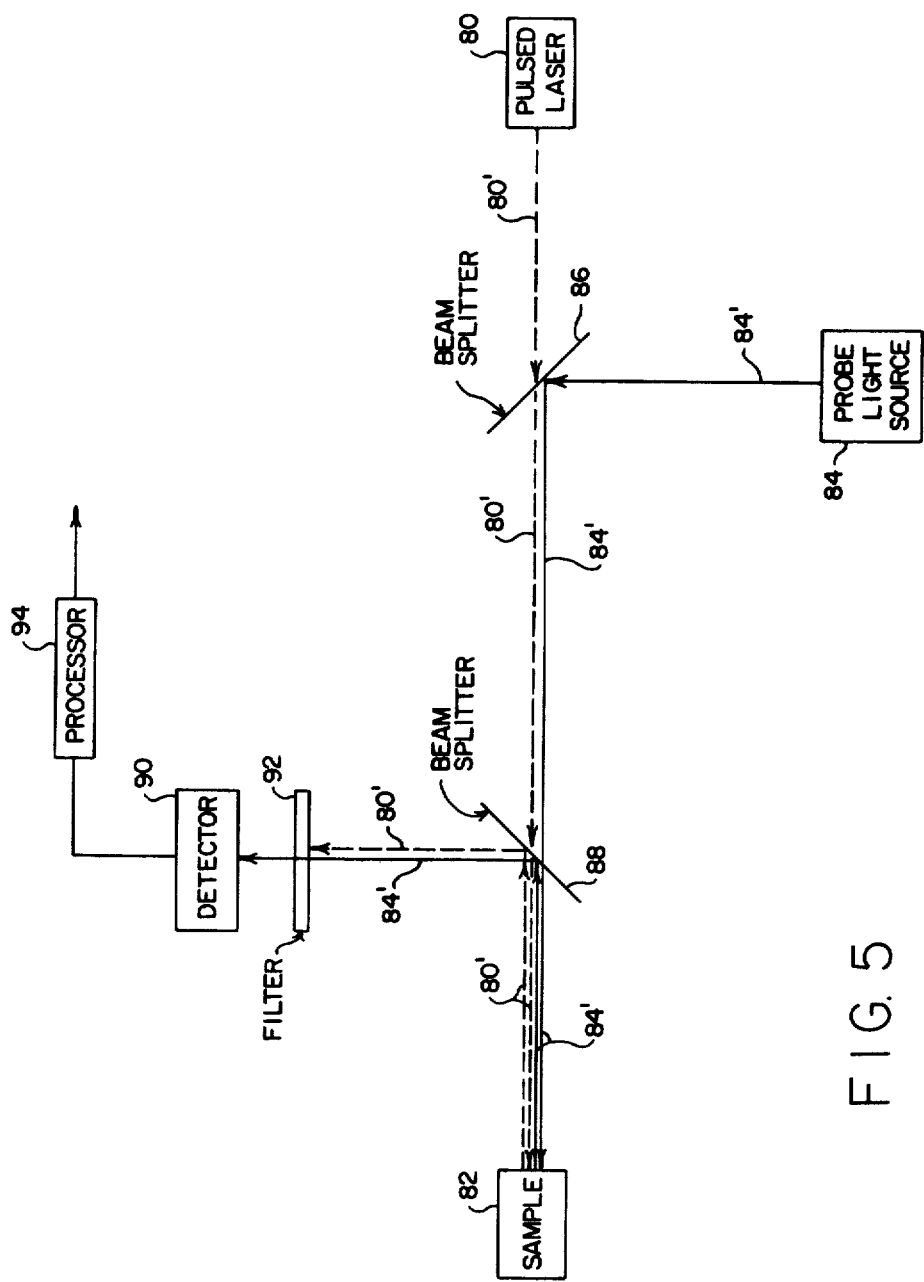
FIG. 5 is a schematic diagram of a third embodiment according to the invention in which the sample material is substantially opaque to the pulsed laser light beam and the probe light beam, and the probe light beam reflected from the sample material is directed to the detector by a beam splitter.

A third embodiment of the invention provides for a sample material which is also opaque to both the pulsed laser light beam and the probe light beam, this embodiment providing a means to detect the probe light beam portion which is reflected back from the sample material along a path colinear with the probe light beam path prior to its irradiation of the sample material. Referring to FIG. 5, a pulsed laser light source 80 provides a pulsed laser light beam 80' which is directed at an opaque sample material 82. A probe light source 84 provides a probe light beam 84' directed to intersect a first beam splitter 86 which in turn reflects a portion of the probe light beam 84' so that it is colinear with the pulsed laser light beam 80'. The pulsed laser light beam 80' and probe light beam 84' then passes through a second beam splitter 88, the pulsed laser light beam 80' forming a thermal lens in the sample material 82 within a few microns of the surface as previously explained. Portions of the probe light beam 84' and the pulsed laser light beam 80' are reflected from the sample material 82, and the thermal lens formed therein, back along the path of the incoming light beams 80' and 84' and to the second beam splitter 88. The second beam splitter 88 reflects a portion of both the probe light beam 84' and the pulsed laser light beam 80' to a detector 90. As in the previous embodiments, a pulsed laser light beam filter 92 is provided for absorbing energy at a wavelength corresponding to that of the pulsed laser light beam 80'. The intensity versus time profile developed by each detector element of the detector 90 is then combined by a processor 94 which in turn provides a composite intensity versus time profile associated with each detector element. As in the first embodiment, the detector 90 can have any of the configurations as previously explained in conjunction with the discussion relating to FIG. 3.

An apparatus provided by the invention operates as follows. Referring again to FIG. 1, the pulsed laser light source 10 must be chosen so that the energy contained within each pulse can be absorbed by the sample material 18 to form the thermal lens therein, and the time between pulses must be chosen so that the thermal lens formed by each pulse can substantially dissipate prior to the arrival of the next pulse. In one specific application of the invention the thermal diffusivity of polymethylmethacrylate (PMMA) was measured. For this measurement, a pulsed laser light source 10 was chosen to be a dye laser having a pulse width of 10 nanoseconds and a wavelength output variable between 360 and 380 nanometers. The pulse repetition rate was approximately 500 pulses per minute or 120 milliseconds between pulses. Using the above-described pulse in conjunction with PMMA, it is theorized that approximately $10^{-8}$ joules per pulse will be deposited in the volume increment where the thermal lens is to be formed, the volume increment being theorized to be less than $10^{-5}$ cubic centimeters. It is also theorized that the temperature rise in the vicinity of the thermal lens will be $10^{-3}$ degrees Kelvin or less. By using the dye laser at an output wavelength of 380 nanometers, thermal diffusivity of PMMA using an apparatus according to the invention was calculated to be $1.0 \times 10^{-3}$ cm$^2$sec$^{-1}$ which is comparable to that obtained by the National Bureau of Standards which was $1.06 \times 10^{-3}$ cm$^2$sec$^{-1}$.

Figure 6:
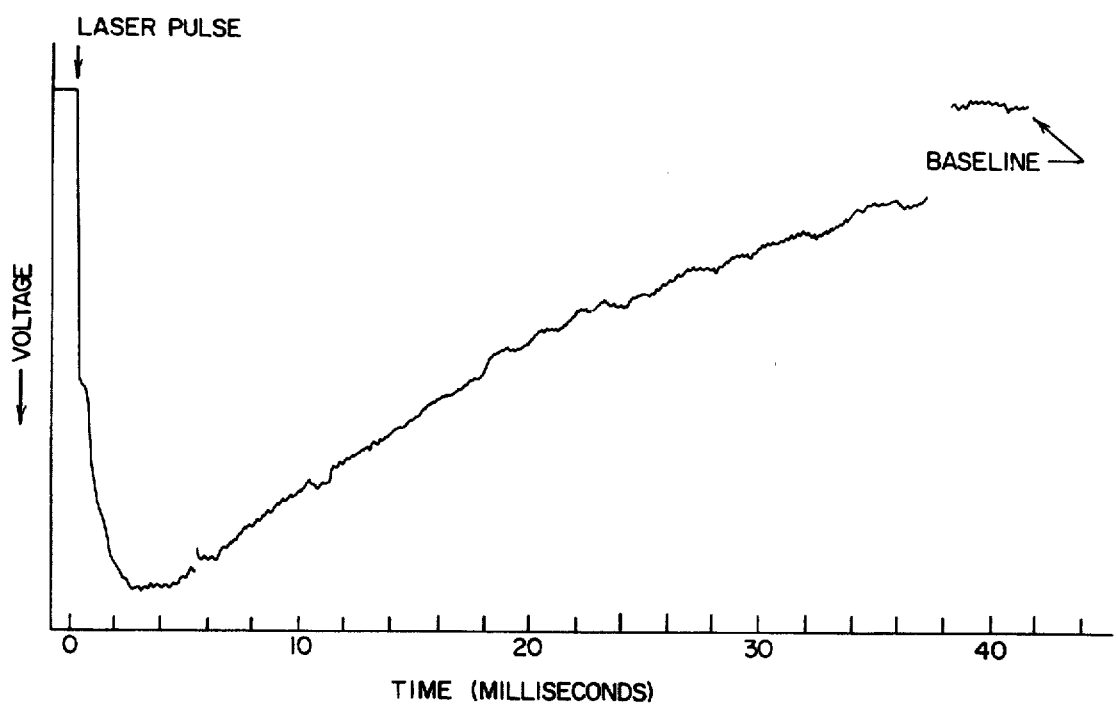
FIG. 6 is a graph showing the intensity of transmitted radiation versus time during the formation and dissipation of a thermal lens created by a laser pulse.

Referring to FIG. 6, the characteristics of a thermal lens formed in PMMA using a dye laser pulse as above-described can be seen to substantially decay to a baseline value in slightly over 40 milliseconds. The voltage shown on the ordinate of the graph of FIG. 6 is related to the output of a single light intensity element comprising the detector 14 and represents an average of 5000 individual profiles. The shape of the intensity versus time profile shown in FIG. 6 is related to the thermal diffusivity of the region surrounding the thermal lens. As one can appreciate, by appropriately choosing and focusing pulses from the dye laser 10 onto the sample 18, the thermal diffusivity of various layers of the sample can be determined, the particular layer being a function of the focal point of the dye laser. Thus, one can appreciate that by using an apparatus and method according to the invention, thermal diffusivity can be determined for samples undergoing stress tests, samples which are shock sensitive, as well as samples having isotropic or anisotropic characteristics. In addition, this type of test is non-destructive and can generate accurate data using samples having temperature gradients less than $10^{-3}$ degrees Kelvin. In materials substantially opaque to the pulsed dye laser wavelength, an analysis of the change in index of refraction due to the thermal lens, as measured by the probe light beam, becomes more complex since radiation losses as well as conduction and convection losses must be considered. However, the analysis principle is the same although a more sophisticated mathematical treatment of the FIG. 6 type intensity versus time profile is required.

Molecular relaxation characteristics can also be measured using the apparatus provided by the present invention. However, these relaxation characteristics are determined from the formation characteristics of the thermal lens, as contrasted to the diffusivity characteristics of the material which are determined from the dissipation characteristics of the thermal lens. Excitation by means of the pulsed dye laser creates electronically excited states of specific chromophores which undergo radiationless decay followed by vibrational lattice relaxation processes. These relaxation processes depend on the molecular architecture of the lattice structure. This new optical technique to probe lattice relaxation processes differs from the well-known mechanical or dielectric techniques in that here the system is perturbed locally with electronic energy. The locale of the perturbation is determined by control of the exciting light spectrum.

Figure 7:
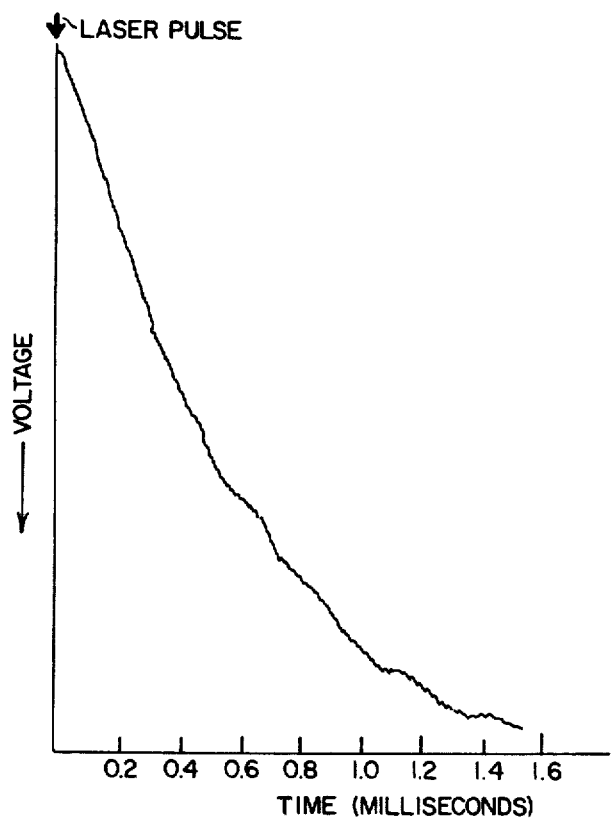
FIG. 7 is a graph showing the intensity of transmitted radiation versus time during the formation of a thermal lens created by a laser pulse.

Using the apparatus and sample material described in conjunction with FIG. 6 above, the formation characteristics of the thermal lens are shown in the composite profile of FIG. 7, the profile again being the average of a plurality of an intensity versus time curves formed as a result of successive pulses from the dye laser. Analysis of the FIG. 7 composite profile comprises a means for determining the molecular relaxation characteristics of the sample material.

Thus as one can appreciate, the invention provides a method and apparatus for measuring both thermal diffusivity and molecular relaxation characteristics of either an isotropic or anisotropic material which is either substantially transparent or substantially opaque to light sources utilized in the apparatus. A thermal lens is repeatedly formed and dissipated in a sample material, each lens being formed by a pulse from a pulsed laser. A change in the index of refraction of the material due to formation and dissipation of the thermal lens is measured by a probe light beam, the light beam being either from an incandescent source or a laser source. The intensity of the light beam versus time as it is affected by the thermal lens during its formation and dissipation provides intensity versus time profiles which are analyzed to determine molecular relaxation characteristics and thermal diffusivity of the sample material.

What is claimed is:

1. An apparatus for measuring thermal diffusivity of a sample material comprising:
    a pulsed laser light source for providing a pulsed laser light beam directed to irradiate said sample material whose thermal diffusivity is to be measured, said pulsed laser light beam characteristics being chosen to cause formation of a thermal lens in said sample material;
    a probe light beam source for providing a probe light beam directed to irradiate said thermal lens;
    a probe light beam focusing lens located between said probe light beam source and said sample material, said focusing lens providing a converging/diverging beam with a focal point at a predetermined location with respect to said thermal lens thereby resulting in an intensity alteration of said probe light beam as a result of irradiating said thermal lens; and
    means for detecting the intensity of at least a portion of said probe light beam after having irradiated said thermal lens during a portion of the dissipation time of said thermal lens, thereby providing an intensity versus time profile related to the thermal diffusivity of said sample material.

2. The apparatus of claim 1 in which said sample material is substantially transparent to said pulsed laser light beam and said probe light beam, and said focusing lens focal point is chosen to lie between said probe light beam source and said thermal lens, thereby resulting in a defocusing of said probe light beam at said detecting means as a result of said probe light beam passing through said thermal lens.

3. The apparatus of claim 1 in which said sample material is substantially transparent to said pulsed laser light beam and said probe light beam, and said focusing lens focal point is chosen to lie between said thermal lens and said detecting means, thereby resulting in a further focusing of said probe light beam at said detecting means as a result of said probe light beam passing through said thermal lens.

4. The apparatus of claim 1 in which said probe light beam source is a cw laser.

5. The apparatus of claim 1 in which said detecting means is a photodiode.

6. The apparatus of claim 1 in which said detecting means is a photon counter.

7. The apparatus of claim 1 in which said detecting means is an area sensitive optical multichannel analyzer.

8. The apparatus of claim 1 in which said pulsed laser light source is a dye laser.

9. The apparatus of claim 1 further comprising a filter substantially opaque to said pulsed laser light beam, said filter being located in front of said detecting means so as to intercept any of said pulsed laser light beam which would otherwise irradiate said detecting means.

10. The apparatus of claim 1 further comprising a processing means whereby successive intensity versus time profiles from said detecting means corresponding to successive pulses from said pulsed laser light source are combined to form a composite intensity versus time profile related to the thermal diffusivity of said sample material.

11. An apparatus for measuring thermal diffusivity of a sample material comprising:
- a pulsed laser light source for providing a plurality of laser light pulses directed at a sample material, the duration of each pulse being chosen so that each pulse forms a transient thermal lens in said sample material, and the repetition rate of said pulses being chosen so that each thermal lens formed is substantially dissipated before generation of the next pulse;
- a probe light beam source for providing a probe light beam directed to irradiate said thermal lens during at least a portion of the time said thermal lens is dissipating;
- a probe light beam focusing lens located between said probe light beam source and said sample material, said focusing lens providing a converging/diverging beam with a focal point at a predetermined location with respect to said thermal lens, thereby resulting in an intensity alteration of said probe light beam as a result of irradiating said thermal lens; and
- detecting means for providing a plurality of intensity versus time profiles corresponding to a plurality of positions within a portion of said probe light beam after having irradiated said thermal lens, said plurality of intensity versus time profiles being related to the thermal diffusivity of said sample material.

12. The apparatus of claim 11 further comprising a processing means for forming a plurality of composite intensity versus time profiles corresponding to each of said positions, each of said composite profiles being formed from a plurality of intensity versus time profiles formed by a corresponding predetermined plurality of successive laser light beam pulses.

13. The apparatus of claim 12 in which said probe light beam source is a cw laser.

14. An apparatus for measuring molecular relaxation characteristics of a sample material comprising:
- a pulsed laser light source for providing a pulsed laser light beam directed to irradiate said sample material whose molecular relaxation characteristics are to be measured, said pulsed laser light beam being chosen to cause formation of a thermal lens in said sample material;
- a probe light beam source for providing a probe light beam directed to irradiate said thermal lens;
- a probe light beam focusing lens located between said probe light beam source and said sample material, said focusing lens providing a converging/diverging beam with a focal point at a predetermined location with respect to said thermal lens, thereby resulting in an intensity alteration of said probe light beam as a result of irradiating said thermal lens; and
- means for detecting the intensity of at least a portion of said probe light beam after having irradiated said thermal lens during the formation of said thermal lens, thereby providing an intensity versus time profile related to the molecular relaxation characteristics of said sample material.

15. The apparatus of claim 14 in which said probe light beam source comprises a cw laser.

16. The apparatus of claim 14 further comprising a processing means whereby successive intensity versus time profiles from said detecting means corresponding to successive pulses from said pulsed laser light source are combined to form a composite intensity versus time profile related to the molecular relaxation characteristics of said material.

* * * * *